United States Patent [19]

Marshall, III

[11] Patent Number: 4,906,576
[45] Date of Patent: Mar. 6, 1990

[54] HIGH SPEED, HIGH POWER APPARATUS FOR VESICLE PREALIGNMENT, PORATION, LOADING AND FUSION IN UNIFORM ELECTRIC FIELDS AND METHOD THEREFOR

[75] Inventor: John Marshall, III, Boulder, Colo.

[73] Assignee: Electropore, Inc., Boulder, Colo.

[21] Appl. No.: 47,208

[22] Filed: May 8, 1987

Related U.S. Application Data

[63] Continuation-in-part of Ser. No. 861,534, May 9, 1986, abandoned.

[51] Int. Cl.[4] .................. C12N 13/00; C12N 15/00
[52] U.S. Cl. ............................... 435/287; 435/173; 435/172.1; 935/52; 935/85
[58] Field of Search ............... 435/172.1, 173, 287, 435/289; 204/180.1, 299 R, 183.3

[56] References Cited

U.S. PATENT DOCUMENTS

| | | |
|---|---|---|
| 4,081,340 | 3/1978 | Zimmerman et al. |
| 4,289,756 | 9/1981 | Zimmerman . |
| 4,441,972 | 4/1984 | Pohl . |
| 4,476,004 | 10/1984 | Pohl .............................. 204/299 R |
| 4,578,167 | 3/1986 | Schoner . |
| 4,578,168 | 3/1986 | Hoffmann . |

FOREIGN PATENT DOCUMENTS

| | | |
|---|---|---|
| 04336461 | 4/1981 | Fed. Rep. of Germany . |
| 3027604 | 2/1982 | Fed. Rep. of Germany ...... 435/173 |
| 213360 | 9/1984 | German Democratic Rep. . |

OTHER PUBLICATIONS

"Hemolysis of Human Erythrocytes by a Transient Electric Field", Kinosita & Tsong, Proc. Natl. Acad. Sci. USA, vol. 74, No. 5, pp. 1923–1927, May 1977.
"Use of Voltage Pulses for the Pore Opening and Drug Loading, and the Subsequent Resealing of Red Blood Cells", Kinosita & Tsong, Biblthca Haemat, No. 51, pp. 108–114.
"Formation and Resealing of Pores of Controlled Sizes in Human Eurthyrocyte Membranes", Kinosita & Tsong, Nature, vol. 268, 4 Aug. 1977.
"Reversible and Irreversible Modification of Erythrocyte Membrane Permeability by Electric Field", Sepersu, Kinosita & Tsong, Biochimica et Biophysica Acta 812, pp. 779–785.
Dielectrophoresis, by F. Pohl, Cambridge Press, 1978.
"Cell Fusion Induced by High Electric Impulses Applied to Dictyostelium", by E. Neumann et al., Naturwissenchaften 66, S. 414 (1980).
"Fusion of Avena Sativa Mesopyhyll Protoplasts by Electric Breakdown", Biochima et Biophysica Acta, 641 (1981, pp. 160–165), by U. Zimmerman et al.
"Hemolysis of Human Ertyhrocytes by a Transient Electric Field", by Kinosita & Tsong, Proc. Natl. Acad. Sci., USA, vol. 74, No. 5, pp. 1923–1927, May 1977.
"Use of Voltage Pulses for the Pore Opening and Drug Loading, and the Subsequent Resealing of Red Blood Cells", by Tsong & Kinosita, Biblthca Haemat, No. 51, pp. 108–114 (Karger, Basel 1985).
"Formation and Resealing of Pores of Controlled Sizes in Human Erythrocyte Membranes", by Kinosita and Tsong, Nature, vol. 268, 4 Aug. 1977.
"Effects of High Electric Fields on Micro-Organisms", by J. H. Sale, W. A. Hamilton, Biochimica Et Biophysica Act A 163 (1968), 37–43.

(List continued on next page.)

Primary Examiner—T. Tung
Assistant Examiner—John S. Starsiak, Jr.
Attorney, Agent, or Firm—Dorr, Carson, Sloan & Peterson

[57] ABSTRACT

A high speed, high voltage apparatus using homogeneous, uniform electric fields to treat vesicles carried in a suspension. In one embodiment, parallel electrodes are used to perform dielectrophoretic bunching, rotational prealignment, electro-fusion, and poration of vesicles. In another embodiment, a magnetic electrodeless apparatus is used to perform the treatment. Both embodiments are driven by a high speed, high voltage electronic supply system that utilizes a triggered ionization breakdown delivery system.

18 Claims, 7 Drawing Sheets

OTHER PUBLICATIONS

"The Effect of Encapsulation in Red Blood Cells on the Distribution of Methotrexate in Mice", by U. Zimmerman and G. Pilwat, J. Clin. Chem. Clin. Biochem, vol. 16, 1978, pp. 135–144.

"The Maxwell–Wagner Dispersion in a Suspension of Ellipsoids", by Fricke, Walter B. James Lab. of Biophysics, Biological Lab., Cold Spring Harbor, N.Y. 4-1-4-53.

"Reversible and Irreversible Modification of Erythrocyte Membrane Permeability by Electric Field", by Serpersu et al., Biochima et Biophysica Acta 812 (1985), 779–785.

"The Behavior of Unicellular Organisms in an Electromagnetic Field", by Teixeira–Pinto, Experimental Cell Research 20, 548–564 (1960).

"Characterization of Electric Field-Induced Fusion in Erythrocyte Ghost Membranes", by Sowers, The Journal of Cell Biology, vol. 99, Dec. 1984.

Electric–Field Induced Cell–Fusion, U. Zimmerman and J. Vienken, J. Membrane Biol., 67, 165–182 (1982).

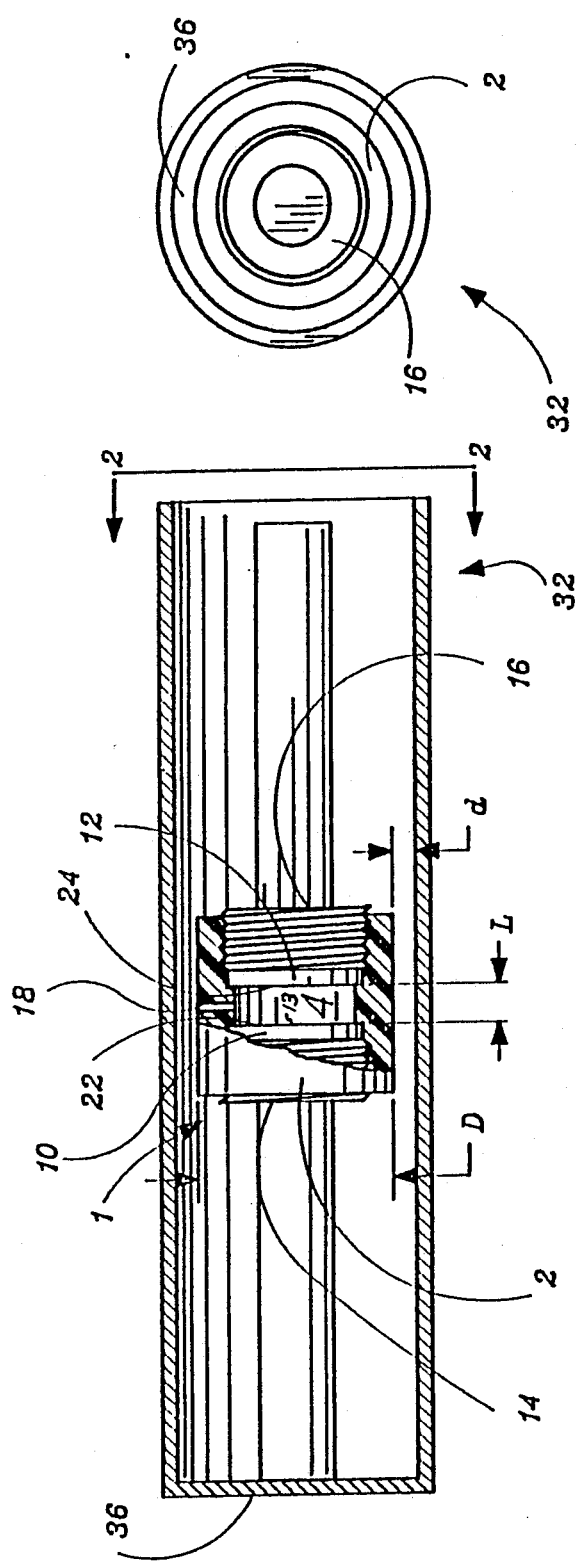
FIG. 2
FIG. 1
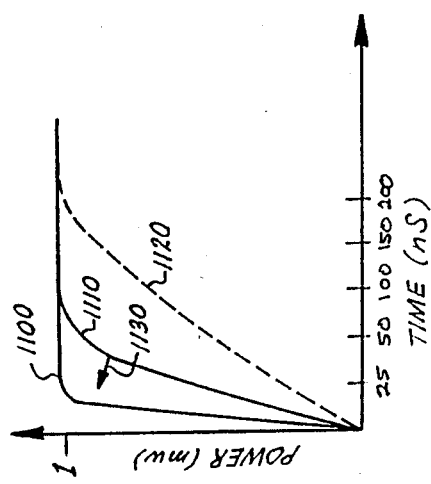
FIG. 11
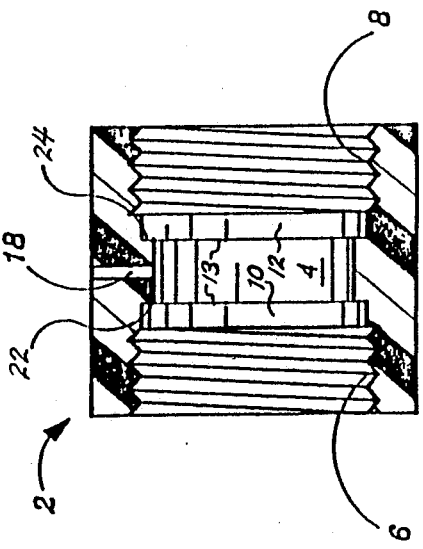
FIG. 3

HIGH SPEED, HIGH POWER APPARATUS FOR VESICLE PREALIGNMENT, PORATION, LOADING AND FUSION IN UNIFORM ELECTRIC FIELDS AND METHOD THEREFOR

RELATED APPLICATIONS

This invention is a continuation-in-part of U.S. patent application Ser. No. 861,534 filed May 9, 1986, now abandoned.

BACKGROUND OF THE INVENTION

1. Field of the Invention—This invention relates to apparatuses and methods for use in the treatment of biological and non-biological vesicles which utilize electric field pulses to prealign vesicles, to introduce pores in and through the membranes of vesicles for the purpose of loading or unloading materials into or from the vesicles or for the purpose of fusing of two or more vesicular structures together and, in particular, to apparatuses and methods which utilize homogeneous and uniform electric fields to treat vesicles.

2. Description of the Prior Art—It is known that stable pores may be created in cell membranes, or in other vesicles, by the application of electric field pulses across a liquid cell suspension containing the vesicles. This is referred to as "poration" or "electroporation".

In such poration processes, cells are suspended in any liquid media, electrolyte, non-electrolyte, or mixtures of electrolytes and non-electrolytes and then subjected to an electric field pulse. Pulse lengths, that is the time that the electric field has been applied to such cell suspensions, have varied in length, for example anywhere from about 10 nanoseconds to about 100 milliseconds. The strength of the electric fields applied to suspensions during such poration processes has varied from between about 100 V/cm to about 30 KV/cm. Sale and Hamilton, "Effects of High Electric Fields on Micro-Organisms III. Lysis of Erthyrocytes and Protoplasts", Biochimica Et Biophysica Acta, 163 (1968) 37–43. In each instance, in order to create a pore in a cell's outer membrane, the electric field has been applied for such a length of time and at such a voltage that a set potential (a transmembrane potential between about 0.5 volt and about 2.5 volts) has been created across the membrane for a length of time adequate to create a pore in the membrane, as is well known in the art. The electric field created across a 100 angstrom the membrane of a vesicle about at 1 volt transmembrane potential is about 1 megavolt per centimeter.

There are four phenomena taught by the prior art which are relevant to the present invention. The first is the phenomenon of dielectric breakdown, that is, the ability of a high electric field to create a small hole or pore in a thin membrane. Once a vesicle is porated it can be loaded or unloaded.

Zimmerman et al, in U.S. Pat. No. 4,081,340 discloses that the "permeability" of cell membranes of cells in an electrically conductive solution can be increased by pumping them through an aperture separating two discrete volumes of electrolyte solution and two electrodes, wherein the electrodes apply an electric field to the cells as they traverse the aperture. As will be set forth in greater detail below, the present invention does not "increase the permeability" of cell membranes, but rather puts actual holes or pores in cell membranes as taught by Kinosita and Tsong, "Formation and Resealing of Pores of Controlled Sizes in Human Erythrocyte Membrane", Nature, Vol. 268, pg. 438–441, 4 Aug. 1977. In "Hemolysis of Human Erythrocytes by a Transient Electric Field", Proc. Natl. Acad. Sci. USA, Vol. 74, No. 5, pg. 1923–1927, May 1977, Kinosita and Tsong describe the use of a homogeneous, uniform electric field to create pores in the erythrocyte membrane. And, Kinosita and Tsong in Bibliotheca "Use of Voltage Pulses for the Pore Opening and Drug Loading", (Karger, Basel 1985) Haematologica, No. 51, pp. 108–114 further describe pulse poration of red blood cells for drug loading purposes using 1 to 5 KV/cm uniform electric field pulses of 1 to 200 microsecond duration. Whereas Kinosita and Tsong outline apparatus for processing microliter quantities of red blood cells, no provision is made or suggestion of how one would process quantities of cells in the many milliliter range. Their instrumentation is limited to small volumes due to the impedance (200 ohms) of the pulse instrument.

In Zimmerman U.S. Pat. No. 4,289,756 porated cells, especially erythrocytes, are loaded with therapeutic drugs. In being subjected to such loading, the general morphology of the erythrocytes is greatly disturbed so that the erythrocytes are preferentially accumulated in the spleen and liver. Zimmerman et al., "The Effect of Encapsulation in Red Blood Cells on the Distribution of Methotrexate in Mice", J. Clin. Chem. Clin. Biochem, Vol. 16, 1978, pp. 135–144.

The second phenomenon is a dielectrophoretic bunching effect as taught by F. Pohl in his book, *Dielectrophoresis,* Cambridge Press 1978, Chapter 4, pp. 39, which describes the mutual self attraction produced by the placement of vesicles in a uniform electric field. Stolley, German Democratic Republic Patent 0433-6461, 1984, uses the Pohl technique in a system for collecting suspended particles, especially biological cells for the purposes of hybrid cell technology. Stolley's system uses a chamber having parallel electrodes to generate a homogeneous high frequency electric field to produce dielectrophetic bunching. This phenomenon is different from the dielectrophoretic force achieved by attracting vesicles to an electrode through the use of non-homogeneous field generation.

The third phenomenon is that of vesicle fusion, which is taught by E. Neumann et al. in the paper "Cell Fusion Induced by High Electric Impulses Applied to *Dictyostelium*", Naturwissenchaften 67, S. 414 (1980), and also by U. Zimmerman et al. in his paper "Fusion of Avena Sativa Mesophyll Protoplasts by Electric Breakdown," Biochimica et Biophysica Acta, 641 (1981, p. 160–165). These papers describe the tendency for membranes of biological vesicles, each of which have had holes or pores formed by dielectric breakdown, to couple together at their mutual dielectric breakdown sites when two such vesicles are in close proximity. The papers also report the natural resultant joining, or fusing of the two cells into a single cell package.

Another prior art process for fusing cells has been presented in an article appearing in the J. Membrane Biol. 67, 165–182 (1982), Electric Field-Induced Cell-to-Cell Fusion by Zimmermann and Vienken. In this process, disturbances in the membrane structure between neighboring cells are produced by using a penetrating electrical impulse which leads to a cytoplasmic continuum in the membrane contact zone between the two cells and to the creation of a lipid jointure between the membranes of neighboring cells. Due to surface energy reasons, the structure formed as the cells are connected to each other by lipid material is rounded off after a jointure is formed. In order to execute this procedure, a chamber was used which had a volume for containing the cell suspension which is contained by non-conductive walls. At least two metallic electrodes protrude into this area to form a space in which the cells are exposed to an electrical field created by the electrodes. These electrodes are shaped to purposefully generate non-uniform fields. At the same time, the electrodes are connected to a device producing electrical voltage impulses in order to achieve electrical permeation.

In U.S. Pat. Nos. 4,476,004 and 4,441,972 Herbert Pohl describes methods and apparatus for causing electrofusion of biological particles. The descriptions of the process and apparatus in these patents suggest that in order to achieve cell fusion it is required, and of primary importance, to place the suspensions of polarizable cells or vesicles into chambers in which non-homogeneous or non-uniform electric fields are generated.

The fourth phenomenon is the tendency of aspherial cells to line up along one of their axes in the presence of high frequency fields as taught by Teixeira-Pinto et al., "The Behavior of Unicellular Organisms in an Electromagnetic Field", Experimental Cell Research 20, 548–564 (1960).

A process of aligning cells in an electrical field was made known in the Biochimica et Biophysica Acta, 694 (1982), 227–277 "Electric Field-Mediated Fusion and Related Electrical Phenomena, U. Zimmerman". In this process membrane contact between at least two cells is brought about by using an alternating and generally weak inhomogeneous electric field. Dipoles are produced by the electrical fields due to polarization processes in the cell. Such polarized cells display a mutual attraction as the cells draw closer together when migrating in the electrical field, in a form of so-called dielectrophorosis.

In most of the references discussed above, the electric fields utilized are non-uniform using electrode configurations of pin-pin, pin-plate, and wire-wire. See Pohl, *Dielectrophesis, supra* at 356–359. The use of non-homogeneous, non-uniform electric fields for vesicle treatment represents the majority view that vesicles more properly are treated by the actual non-uniformity of the fields. Yields, such as for poration, unfortunately are low. A minority view, expressed in the Kinosita and Stolley references, supra, utilize homogeneous, uniform-therein electric fields using parallel plate electrodes for the limited treatment o f vesicles . Stolley performs dielectrophoretic bunching and Kinosita performs poration and loading of vesicles.

The apparatuses and methods of the present invention utilize homogeneous, uniform electric field generation for treatment of biological and non-biological vesicles including prealignment of vesicles, poration of vesicles, loading of vesicles (and unloading) and fusion of vesicles. The present invention improves upon the teachings of Stolley and Kinosita by providing: (a) rotational prealignment to increase the uniformity of poration of vesicles and the loading of vesicles over a whole sample providing high yield rates, (b) collection of vesicles in a uniform, homogeneous electric field in conjunction with a fusion pulse also generated uniformly and homogeneously, (c) processing of much greater volumes of vesicles and in much lower conductivity suspensions by switching large power signals at very fast switching times, and (d) an apparatus for magnetically producing uniform, homogeneous electric fields in an electrodeless chamber. None of these features of the present invention are found in any of the prior art references.

SUMMARY OF THE INVENTION

The present invention, therefore, relates to methods and apparatuses for use in vesicle rotational prealignment, in vesicle bunching, in dielectrophoretic electroporation of vesicles, in cell hybridization (fusion), and in vesicle loading and unloading.

The present invention provides a solution to the prior art problem of only obtaining low yield rates in the treatment of vesicles and the prior art problem of being able to treat small volumes of vesicles especially in high-conductivity suspensions.

The chamber of the present invention is designed to contain large volumes of suspensions of living cells or other suspended living or non-living vesicles. Furthermore, high speed, high power pulses of electric charge or field can be uniformly and homogeneously applied throughout the entire suspension, excepting the actual imhomogeneties to the field created by the cells themselves, to uniformly treat (i.e., to prealign,, to bunch, to porate, to fuse, etc.) large numbers of the vesicles.

As will be seen in greater detail below, the present apparatus and method is an identifiable departure from the scope and the spirit of the inventions described in Pohl U.S. Pat. Nos. 4,441,972 and 4,476,004, and from other references which mandate the application of a non-homogeneous, non-uniform electric field to treat vesicles. Further, the present invention improves upon the teachings of Stolley and Kinosita and their limited use of uniform electric fields. The present invention also applies the principle of the attractive polarization of cells which have been placed in uniformly generated high frequency electrical fields, which attraction is due to the fact that such cells produce attractive forces between one another as a result of the reformation of the uniform electric field caused by the presence of the cells themselves.

In order to achieve these results, the pulse chamber of the present invention will consist, in general, of two preferred embodiments: (a) two spaced-apart, parallel electrodes and (b) an electrodeless hollow toroidal disposable chamber. In the parallel plate embodiment, the electrodes are preferentially circular in cross-section and cap the ends of a cylindrical chamber, thus defining a cylindrical volume between them. In preferred embodiments, the volume of the cylinder will measure anywhere between about 0.5 milliliters and about 100 milliliters. The two spaced-apart electrodes will, when subjected to an electric charge, create a uniform, homogeneous electric field across a test (particle-free) electrolyte solution located in the cylindrical gap between them.

The cylinder intermediate to the electrodes will be composed of electrically insulating material, such as glass, plastic or other non-conductive material with a low dielectric constant. The exposed surfaces of the conductive electrodes which reside within the chamber cavity will preferably be composed of a material, such as platinum or gold, which is selected to minimize or prevent electrolytic decomposition of the vesicles of suspension on the electrodes in the chamber during electrical treatment. Electrical coupling contact between the electrodes of the pulse chamber and an electrical treating system are made, for example, using clips or clamping devices to each electrode, although permanent connections may also be made.

When the pulse chamber is of the toroidal configuration, uniform electric field coupling is produced magnetically by running a charging magnetic flux axially through the annulus of the toroid. The electrodeless magnetic chamber of the present invention therefore avoids the decomposition problem of the aforesaid parallel plate electrode approach and provides a convenient disposable chamber.

Under the teachings of the present invention, in order to be able to make precision, high speed application of high voltage across and high current through the chamber, the inductance and capacitance of the chamber are chosen to match the impedance of the electrical source. This impedance matching will be accomplished, for example, by providing a coaxial or biaxial current feed path to the electrodes.

Since the conductivity of the various suspensions placed into the pulse chamber varies widely, the electric charge source is designed to deliver a large range of currents, anywhere from about 0.1 ampere to about 100,000 amperes, depending upon the conductivity and amount of the pulsed suspension. The delivery of high voltages also requires sophisticated switching techniques, as taught by the present invention. In preferred embodiments, the high voltage source will be connected to the chamber through a triggered ionization breakdown such as that achieved with a moving spark gap (such as a gas filled relay), gas filled spark gap, vacuum spark gap, ignitron, high current series SCR stacks, or hot or cold cathode hydrogen thyratrons, as will be set forth in greater detail below. In certain situations, such as the treatment of large volumes of suspensions, cold or hot cathode hydrogen thyratrons, ignitrons, spark gaps, or vacuum spark gaps are especially useful as switches.

The present invention therefore is capable of delivering at high speeds (i.e., less than 50 nanoseconds) high current and high voltage electric field charges (i.e., at a power rate greater than 1 Megawatt) uniformly and homogeneously over large volumes (i.e., greater than 1 milliliter) of suspensions containing vesicles to be treated. None of the prior references set forth a system for delivering such power levels, at such speeds, to such quantities of such highly conductive suspensions. For example, the electrical driving mechanism of Kinosita was a Cober 605P pulse generator having a maximum output of 2200 volts at 11 amps, and not being able to drive resistive or capacitive loads with impedances less than 20 ohms while maintaining rise time. The present invention is capable of delivering up to 35,000 volts at currents up to 100,000 amperes in less than 50 nanoseconds.

The system of the present invention may optionally be used in conjunction with a high frequency random function generator for producing cell rotational alignment prior to poration. Rotational alignment is the creation of torques on cells or other vesicles in suspension in the pulse chamber by means of high-frequency polarization of the suspended material. In the present invention, rotational alignment will be accomplished utilizing a timer which will allow the controlled connection of a high-frequency electric field at selected voltage and frequency across the pulse chamber prior to poration treatment.

In preferred embodiments, where cell fusions are desired, the dielectrophoretic bunching voltage will be applied across the pulse chamber long enough, and at a predetermined frequency, to maximize the number of cell pairs that are formed in the chamber. To this end, more than one dielectrophoretic high frequency electric field may be applied by use of a random function generator under the teachings of the present invention. Then, after dielectrophoresis treatment is completed, the application of a high voltage pulse to the suspension will create mutual pores between pairs of conjoint vesicles. In a high percentage of such cases each pair of porated cells will fuse into one cell after a short period of time, generally about 1 to 20 minutes.

The size of the pores created in cells or other vesicles will be controlled under the teachings of the present invention by varying three parameters of electric field exposure: pulse voltage, pulse duration, and rate of change of electric field rise time and fall time. Since the membrane of each type of cell or other vesicle will have characteristic elements of resistance and capacitance, each type of cell or vesicle will exhibit a characteristic time constant related to the resistance and capacitance of the cell's membrane or the vesicle's skin. The specific time constant of any cell membrane will be governed basically by a multiple of resistance and capacitance:

$$ti\ t = R(C) \qquad \text{(Formula 1)}$$

where, R is measured in ohms and C is measured in microfarads. The time constant will in part determine the rate at which a voltage will be developed across a specific cell membrane. Thus, for example as taught herein, specific cells having specific time constants or various membrane contained subunits of cells (i.e., the nuclear membrane chloroplasts) will be capable of being selectively porated after determination of their time constant. In the practice of the present invention there is no need to increase the permeability of cell membranes, as taught by U.S. Pat. No. 4,081,340. The method and apparatus of the present invention create actual holes or pores of controllable size in and through the membrane of the vesicle, whether biological or non-biological, rather than merely changing the permeability of the membrane.

The capacitances of cell membranes, are usually on the order of 1 microfarad per square centimeter of membrane. As the salinity of intracellular and extracellular solutions increases, however, the resistance of the membrane per unit area is likely to decrease. This requires in turn a faster rise of surrounding electric field such that transmembrane potential does not "bleed off" across the transmembrane resistance so quickly as to keep the membrane from reaching poration potential. Also, the smaller a cell is, the faster the rise time necessary to reach a specific transmembrane potential. A red blood cell is a very small mammalian cell. To maintain morphology, one maintains it in a low-resistance isotonic solution. It is a good example of a cell needing specialized high-power, fast rise time pulse techniques as taught by the apparatus of the present invention to achieve poration when porating milliliter or greater quantities of these cells.

To load substances into cells, the porated cells will be left in the suspension with open pores and stored at cool to ambient temperatures for a period of time. The present invention loads cells with substances by first creating stable holes or pores in them, and then, much in the manner taught by Kinosita and Tsong, supra, lets intracellular and extracellular fluids intermix by passive diffusion and Brownian motion through the pores. This will result in the equilibration of the mixture within the cells and outside of the cells if the pores are left open long enough. Cells can also be porated in an isotonic solution, centrifuged down, separated, and then resuspended in a solution which is to be loaded into the cells. Pores in cell membranes will then be resealed after a period of time at ambient temperature, or by gently heating them to some non-destructive temperature greater than ambient, most usually 37 degrees C.

For fusion of cells, high frequency alternating homogeneously generated electric fields are applied across the cell suspensions to create mutual dielectrophoresis or bunching as taught by *Teixeira-Pinto*, supra, and by Pohl, *Dielectrophoresis*, supra. Under the teachings of the present invention, after pairs of cells are formed, a high intensity electric field pulse, say for 100 microseconds or less will be applied, with the result that dielectric breakdown occurs at contiguous adjacent points on the aggregated pairs of cells, with the result that cell fusion will occur, as taught by the prior art. The cells will then typically fuse into single cells, usually no longer than about twenty minutes after the poration event. Then the cells can then be heated to ambient temperatures or greater, (e.g., to about 37 degrees Celsius) to close or "anneal" the membrane. In any event, temperatures which would cause damage to cells are avoided.

When cells undergoing treatment are not spheres or are not electrically or dielectrically spherical, but are aspherical, ellipsoidal or electrically or dielectrically aspherical in nature, they are generally distributed in random orientation in the suspension. Even where cells are structurally spherical, they may still be electrically aspherical due to cell membrane charge imbalances. Such cells will have a long axis and a short axis or a polarity, and as such, when a porating electric field is applied, differing transmembrane potentials develop, depending on which orientation of the cell is exposed to the electric field. This creates a problem if one wishes to uniformly porate all cells in the suspension. As application of the pulse across randomly oriented cells would produce proper poration on only a percentage of the cell population.

This problem will be resolved, according to the teachings of the present invention by pre-aligning the asymmetrical cells into a similar orientation, so that all of the cells can be subjected to the same transmembrane poration electric field pulse. Prealignment will be accomplished for such cells in a suspension by applying an electric field having a selected high frequency across the electrodes for a short interval prior to the application of a poration pulse as taught in Pohl, pp. 40–47, supra, and in "The Maxwell- Wagner Dispersion in a Suspension of Ellipsoids", Hugo Fricke, Phys. Rev. Vol. 37, pg. 934–937. In such situations there will be two sets of frequency of interest. One set of frequencies will tend to line up the cells along their major axis or polarity, while a second set of frequency will tend to line up cells along their minor axis. This is as taught by Pohl, supra, Chapter 4, Pg. 41–42 (and references cited therein).

Under the teachings of the present invention, along whichever axis the asymmetrical cells are mutually oriented, once they are all aligned along the same axis, they will all experience the same transmembrane potential when exposed to a pulsed homogeneous uniform porating field. This will allow for the uniform poration of substantially all cells that are structurally, electrically, or dielectrically non-symmetrical in nature by the application of the time constant, as set forth above.

In addition to the application of voltages across a suspension between two electrodes, cell membranes may also be porated under the teachings of the present invention by pulsed magnetic field techniques. As detailed below, this will be accomplished by loading an electrolytic cell suspension in a toroidal chamber that is exposed to rapidly changing magnetic flux fields. The flux vector of the magnetic field will be directed through the center of the toroid. This causes an electric gradient field to be generated through the cell suspension loaded in the toroidal chamber. All effects of poration, dielectrophoretic bunching, dielectrophoresis and cell fusion may be achieved; however, voltages generated would now be impressed on a member which will serve much like the primary of a transformer coupling, rather than by impressing the voltage directly on chamber electrodes.

For a fuller understanding of the nature and objects of the invention, reference should be had to the following detailed description taken in connection with the accompanying drawing.

BRIEF DESCRIPTION OF THE DRAWING

The accompanying drawings illustrate complete preferred embodiments of the present invention according to the best modes presently conceived for the practical application of the principles thereof, and in which:

FIG. 1 is a front plan view, partially broken away and partially in cross-section illustrating the electroporation chamber of the present invention;

FIG. 2 is a side view in elevation taken along 2—2 of FIG. 1;

FIG. 3 is an enlarged cross-section of the block portion of the electroporation chamber of FIGS. 1 and 2;

FIG. 11 is a graph illustrating the controllable rise time of the uniform, homogeneous electric field of the present invention.

1. Chamber

Figure 4:
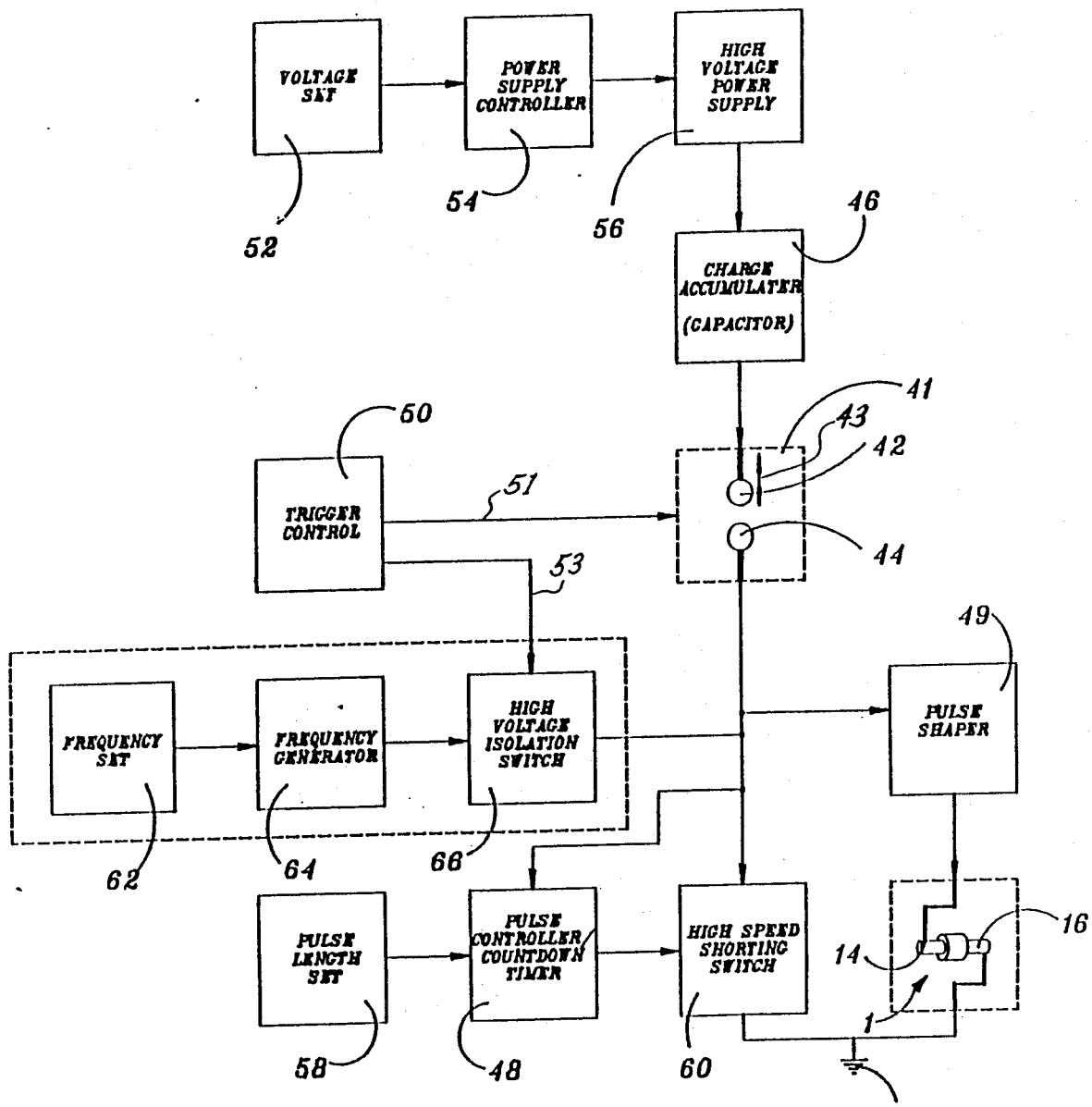
FIG. 4 is a partially schematic, partially diagrammatic representation of the electronic control system of the present invention.

Referring to FIGS. 1, 2, and 3, an electroporation or cell fusion chamber 1 is shown which will apply electric fields uniformly and homogeneously to suspensions containing vesicles or other suspended media. The vesicles in the suspension, of course, will create inhomogeneities to the field.

The chamber 1 includes a block 2 of dielectric material such as polacetyl plastic, which is machined or molded to define a cylindrical central pulse chamber 4, bracketed by opposed threaded open ends 6 and 8 and including shoulders 22 and 24. In preferred embodiments, thread-ended electrodes 14 and 16 will each be screwed into threaded open ends 6 and 8, respectively, towards chamber 4 until they rest against shoulders 22 and 24 respectively, with the result that a fluid tight fit is maintained between the electrodes and the openings into which they are fitted. This tight fit provides a fluid seal to prevent fluid suspensions from leaking from pulse chamber 4 through threading in open ends 6 and 8. A specific distance "L" will be defined and maintained between the ends of electrodes 14 and 16 to define a specific size or volume for pulse chamber 4. In the preferred embodiment shown, a fillhole 18 will be provided through block 2 to pulse chamber 4, to allow addition to or removal of suspensions from pulse chamber 4, for example, by the use of a hypodermic syringe.

The body of each electrode 14 and 16 will be formed of metal or other electrically conductive material. In preferred embodiments electrode tip faces 10 and 12 will be coated with a thin film of gold, platinum, or other inert, stable, conductive material 13, in order to prevent electrolytic decomposition of liquid in the chamber or on the electrodes during electrical pulses. The materials for the chamber and for the electrodes will also be chosen so that sterile conditions can be easily maintained, and preferably are composed of materials which can endure autoclave temperatures.

In operation, suspended cell media 28 (see FIG. 5a) are inserted into pulse chamber 4 through fillhole 18 by use, for example, of a hypodermic syringe, not shown. Once within pulse chamber 4, the suspension will be subjected to treatment, as described below.

In order to minimize the inductance and match impedance of chamber-block 2, the current feed path to electrodes 14 and 16 is coaxial with chamber block 2. Referring to FIGS. 1 and 2, an outer current return path in the form of a cup 32 having a cylindrical conducting shell and closed end 36 is provided. End 36 will be in electrical contact with one electrode, in this case electrode 14, while conducting shell 32 substantially encloses chamber block 2 and electrode 16. The distance "d" between shell 32 and the outer of chamber-block 2 and the distance "D" which is the chamber-block diameter might be adjusted, for example by selecting a cup having the correct dimensions, so that impedance matching of chamber-block 2 to various voltage/current generating sources, can be provided or low inductance can be maintained. When the inductance is minimized, precision, high speed applications of the voltage across and the current through pulse chamber 4 can be made.

2. Electronics

A high voltage connection will be made to chamber 1, for example, with a moving spark gap or high speed switch. As shown diagrammatically in FIG. 4, the spark gap 41 consists, for example, of two spherical electrodes 42 and 44. As detailed below, electrode 42 will be connected to charge accumulator 46, such as a capacitor which will serve as a voltage source to chamber 1 during poration. The accumulator, however, may be any conventional charge storage device.

Spherical electrode 42 will be designed for movement toward and away from electrode 44. In operation, as detailed below, electrode 42 will be moved under control of trigger 50 toward electrode 44 as shown by arrow 43 until a spark is initiated between electrodes 42 and 44. At this point, ionization breakdown between the electrodes quickly occurs and the full power of the charge is delivered to the opposing switch electrode and, thence, to the chamber 1 in less than 50 nanoseconds. This spark serves to connect chamber 1 to charge accumulator 46 through electrode 14. In the embodiment shown in FIG. 4, the instant that a spark is initiated between electrodes 42 and 44, an electronic pulse controller countdown timer 48 is started, as detailed below. Movement 43 of electrode 42 towards and away from electrode 44 will be provided, for example, by the use of a conventional solenoid driver with spring return, not shown.

For cell fusion, moving spark gap 42–44 may be replaced by a high speed switch (e.g., spark gap, thyratrons or ignitrons) so that precision triggering of initial charge is accomplished. The system of the present invention is utilized for dielectrophoretic bunching, poration and/or fusion of suspensions in bunching, poration and or fusion of suspensions in pulse chamber 4.

a. Dielectrophorectic Bunching

Figure 5A:
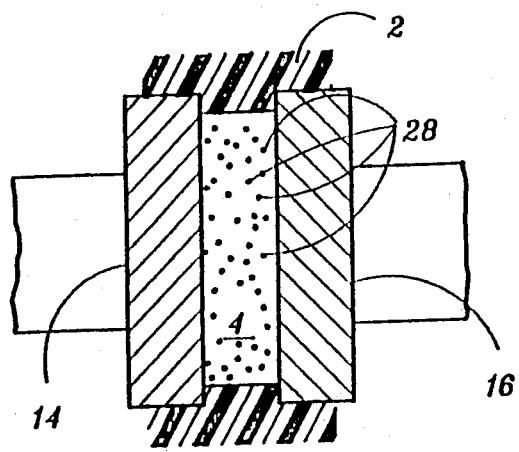
FIG. 5a is a cross-sectional diagrammatic representation of spheroidal cells in a random suspension in a pulse chamber.
Figure 5B:
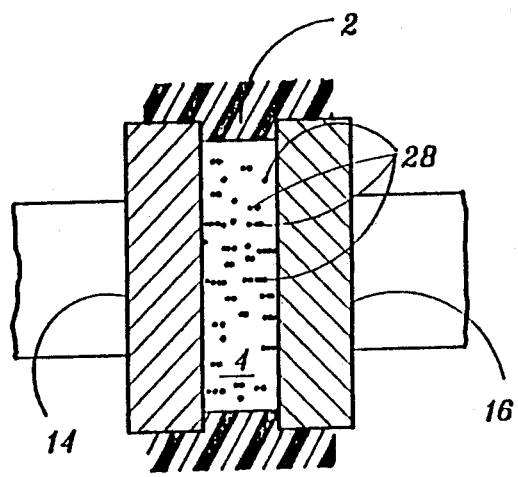
FIG. 5b is a cross-sectional diagrammatic representation similar to FIG. 5a, but with the cells bunched by mutual dielectrophoresis into pairs and pearl chains.

Dielectrophoretic bunching will be accomplished by imposing a high frequency AC electrical field uniformly across the suspension in chamber 4, whereby suspended, randomly distributed vesicles or particles between electrodes 14 and 16, as illustrated in FIG. 5a, attract to one another in a pearl chain, as illustrated in FIG. 5b. This attraction occurs because each vesicle or particle in the suspension will be polarized on each cycle of the applied alternating uniform and homogeneous field. However, vesicles or other particles suspended in pulse chamber 4 will, by their presence, affect the local electric field within chamber 4, with the result that local field inhomogeneities will be formed in what would otherwise be the homogeneous electric field generated between electrodes 14 and 16. This inhomogeneity produces a net force on the suspended vesicle, which force will cause mutual dielectrophoretic attraction between each suspended vesicle and its nearest neighboring vesicles or particles in pulse chamber 4. Thus a marked tendency exists for suspended cells or particles in chamber 4 to line up into pairs or chains either orthogonal or parallel to the two parallel electrode faces 22 and 24 dependent upon the dielectrophoresis voltage frequency or frequencies.

b. Rotational prealignment

Figure 7A:
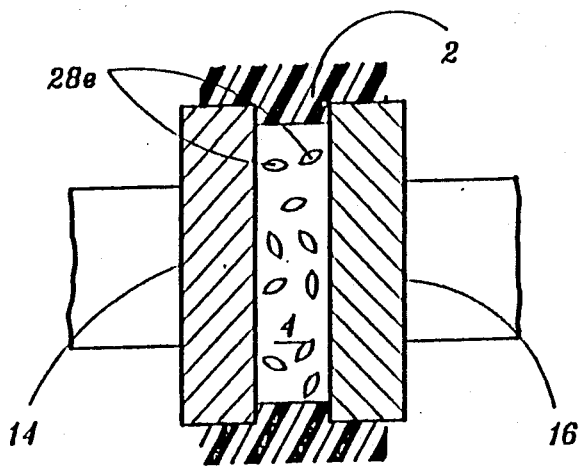
FIG. 7a is an exaggerated cross-sectional diagrammatic representation of ellipsoidal cells in a random suspension in pulse chamber 4.
Figure 7B:
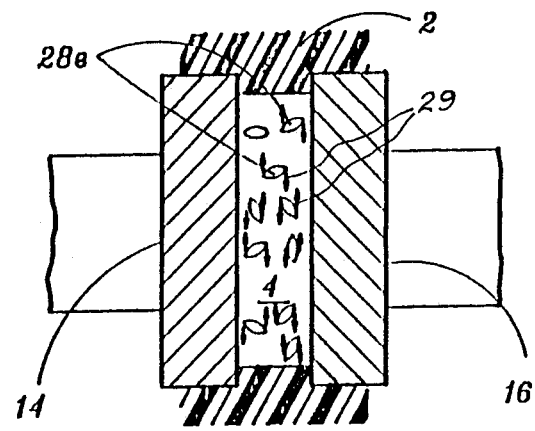
FIG. 7b is a cross-sectional diagrammatic representation, similar to FIG. 7a, in which the ellipsoidal cells are being acted upon by a voltage of an orienting frequency.
Figure 7C:
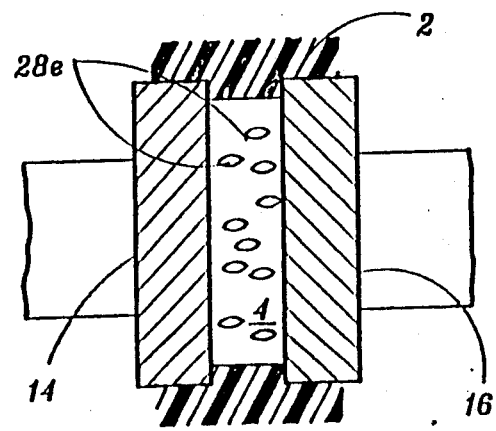
FIG. 7c is a cross-sectional diagrammatic representation, similar to FIG. 7a in which the ellipsoidal cells have been oriented along their major axis.

Non-spherical ellipsoidal) cells will also be subject to being aligned in pulse chamber 4 of the present invention, by the application of the effect known as the Maxwell-Wagner dispersion, supra. For example, as shown in FIGS. 7a, 7b, and 7c, an ellipsoidal cell 28e or particle placed in chamber 4 will experience different rotational forces 29 for different applied frequencies of AC electrical field. However, as taught herein, such particles will be capable of being rotationally aligned in the presence of a uniform, homogeneous high frequency electric field as taught by the present invention. In operation, two frequencies will be of importance for alignment of ellipsoidal cells. There will be at least one frequency that will align such cells between parallel electrode faces 22 and 24 with their major semi-axis orthogonal (90 degrees) to the electrode surfaces. At least one second frequency will align such cells' minor axis orthogonal to the electrode surfaces 22 and 24. By selecting the correct set of alignment frequencies substantially all of the cells of a given type will align on the same axis. When they are pulsed under the teachings of the present invention to cause cell poration, uniform, pore creation will result substantially more homogeneously over the population of the aligned cells. This process will be useful, for example, for purposes of loading materials into single cells e.g. erythrocytes, rather than for inducing cell fusion when used only for times short enough for rotational alignment, but not long enough to produce mutual "dielectrophoretic bunching" attraction as discussed above.

In the preferred operation of the system, in the present invention, extremely high voltage, high current pulses of specific short duration will be passed through electrodes 14 and 16. Such current pulses of a specific length will be created using the high speed switching such as provided by spark gaps, thyratrons, ignitrons, etc. as set forth above.

Referring again to FIG. 4, additional details of the electronic system of the present system are set forth. Several settings must be made by the operator before either electroporation, or electro-fusion are initiated by activating trigger control 50. The high voltage will be selected by the operator at voltage set 52, which, through power supply controller 54, will determine the voltage which will be supplied from high voltage power supply 56 to charge accumulator 46. Accumulator 46 will quickly become fully charged. However, so long as electrode 42 is separated from electrode 44 the electric voltage will not arc to electrode 44 to initiate cell poration in chamber 1. The length of the voltage pulse, once initiated will be determined by the operator at pulse length set 58, through pulse controller/countdown timer 48. Countdown timer 48 will initiate its operation in response to the flow of current through the spark gap between electrodes 42 and 44. When countdown timer 48 reaches zero, it will activate high speed shorting switch 60. Shorting switch 60 will instantaneously impose a short circuit across chamber 1. This short circuit will cause even larger currents to flow from accumulator 46, but will "dump" its entire potential, and dissipate it as heat energy or discharge it to ground 70, to terminate the flow of current through chamber 1. However, at the time that current flow through chamber 1 is initiated, shorting switch 60 must be open in order to allow the current flow through chamber 1. High speed switch 60 may also be a spark gap, ignitron or hydrogen thyratron.

c. Electro-fusion

Where an electro-fusion operation on the cells in chamber 1 is desired, the operator will select one or more frequencies at frequency set 62, through frequency generator 64. The frequency or frequencies will be selected to cause the randomly distributed cells, as shown in FIG. 5a, to dielectrophoretically bunch, attract one another, and to even form pearl chains after a period of time, as shown in FIG. 5b. The selected frequency or frequencies will pass through closed high voltage isolation switch 66. When switch 66 is closed, one or more bursts of high frequency alternating current, each one or more cycle in duration, will be applied to the cell suspension in chamber 1. However, during high voltage poration pulsing from charge accumulator 46, isolation switch 66 will be opened to protect frequency generator 64 from the high voltage poration/fusion pulse.

d. Poration

In a poration operation without cell fusing, chamber 1 has "to-be-treated" cells injected into pulse chamber 4 through fillhole 18. Chamber 1, possibly including shell 32 is then connected to the apparatus via electrodes 14 and 16. Shell 32 is designed for insertion into and easy high current electrical connection with the treating apparatus by means of low resistance mating connectors, not shown. The "to-be-applied" voltage will be selected at voltage set 52 and accumulated in charge accumulator 46. The pulse length is selected at pulse length set 58, but high speed shorting switch 60 is open in order to avoid short circuiting of the current which is applied to the chamber. Also, high voltage isolation switch is opened in order to protect frequency generator 64. After these arrangements and settings have been made, trigger control 50 is activated and electrode 42 begins to move towards electrode 44. Trigger control 50 is connected over lines 51 and 53 to spark gap 41 and to isolation switch 66, respectively. At some point in the movement of electrode 42, the electric potential in accumulator 46 will be sufficient to cause current to jump from electrode 42 to electrode 44. With the start of current flow from electrode 44, treatment of suspended material in chamber 1, and countdown of timer 48 will be simultaneously initiated, and the cells within pulse chamber 4 will undergo poration treatment.

Figure 6:
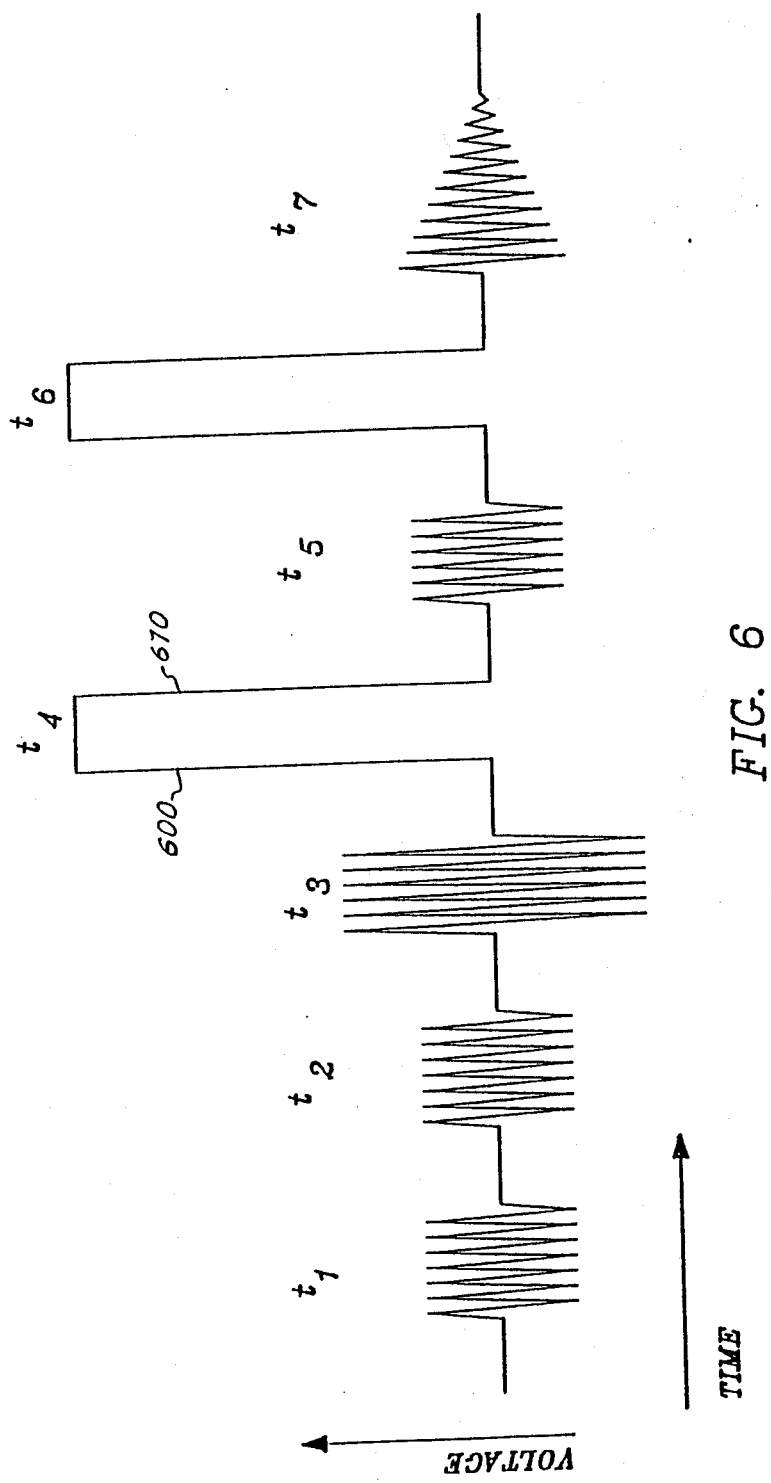
FIG. 6 is a schematic representation of voltage vs. time during various operations of the apparatus of the present invention.

The start of this treatment will correspond to the initial vertical line 600 of t4 in FIG. 6. When countdown timer 48 expires, high speed shorting switch 60 will then be closed, with the result that a short circuit will be imposed across chamber 1. The short circuit will terminate the flow of current through the chamber and stop cell treatment at a time which will correspond to the second vertical line 610 of t4. If desired, the same cells in the same chamber can be subjected to a second electroporation treatment, as at t6 of FIG. 6, in much the same manner and sequence as set forth above. The cells are then removed from pulse chamber 4 by a hypodermic syringe inserted through fillhole 18, and the preponderance of the cells contain stable pores through their cell wall membranes. The porated cells can then be treated, as set forth in the EXAMPLES, below.

The high speed, high current and high voltage system of the present invention can charge up a large amount of aqueous solution with a rise time of less than 50 nanoseconds (1100 of FIG. 11) to produce homogeneous poration in vesicles contained in the suspension.

e. Waveform Examples

In FIG. 6, representative waveforms are shown illustrative of the operation of the present invention in the treatment of vesicles. If cell fusion is desired, substantially all of the same settings will be made in the system as for cell poration, with the exception that the operator will select one or more frequencies at frequency set 62, which frequencies will be selected to orient and/or cause dielectrophoretic coupling and pearl chaining of cells, as shown diagrammatically in FIG. 5b. In this mode of operation, when trigger control 50 is activated, isolation switch 66 will be closed, thus allowing one or more high frequency bursts of alternating current (i.e., waveforms shown at times t1, t2 and t3 in FIG. 6) to be applied to the cells in chamber 1. During these bursts randomly distributed cells as shown in FIG. 5(a) will experience mutual dielectrophoresis or bunching. Nearest neighboring cells will attract one another forming pairs and then, if dielectrophoratic bunching treatment is applied longer, will form chains as shown in FIG. 5(b) and as discussed above. Subsequently, poration treatment will be carried out by the waveform shown at time t4 when the charge crosses from electrode 42 to electrode 44, as described above. If a second poration treatment is to be carried out by the waveform shown at time t6, then one or more intervening dielectrophoretic bunching bursts may be applied, at time t5. When this operation is completed, a current rampdown may be allowed to occur as shown by waveform at time t7. After this operation is completed, then a substantial number of paired, porated cells with mutual pores will fuse into single cells, as described below in the Examples. It will thus be seen that in the practice of the present invention, the circuit of the present invention will permit very high voltage, high current pulses (i.e., greater than 1 Megawatt in power rate) to be applied for accurately controlled lengths of time (i.e., less than 50 nanoseconds) to samples in the pulse chamber 4.

Under the teachings of the present invention, the conductivity of 1 ml of isotonic suspension is such that when suspended in chamber 4 (where L=0.33 cm between the electrodes 14 and 16) the resistance to electrical manipulations that happen in 1 millisecond or faster will be about 15–20 ohms after the first 300 nanoseconds have elapsed. That means that to get an electrical field of 10,000 v/cm a typical field strength for treating cells such as e. coli., a voltage of 3333 volts will have to be imposed across chamber 4. At this resistance, a current of 166 amperes flows to sustain the field. If the chamber with the same electrode spacing had a suspension volume of 100 ml, 100 times the current, or 16,600 amperes would have to flow. The apparatus of the present invention can be scaled up to process vast amounts of solution as long as one uses the aforesaid high voltage, high current, high speed switching techniques, i.e., switches that operate on a spark or fast ionization breakdown and maintains a source impedance that is reasonably matched to load impedance.

The current source including switching must have a very low impedance at these high currents such that all the field drop does not happen in the source. At 16,000 amperes, just 0.1 ohm of impedance would produce a voltage drop of 1600 volts, an unacceptable loss in volume processing. In scaling this further, it can be seen that a volume of 650 ml of isotonic suspension in chamber 4 requires a current of 100,000 amperes to bring the suspension to an electric field stress of 10,000 volts/cm in a chamber with 0.33 cm gap.

In the previous description, the charge accumulator was a low inductance capacitor. The capacitor may also be replaced by a pulse forming network as detailed in FIG. 12. A pulse forming network is a set of equal valued inductors 1200 and capacitors 1210 configured such that when charged to a voltage V by supply 56 and then connected to a load (such as a pulse chamber 4) the network will deliver a fixed length pulse of amplitude V/2.

Figure 12:
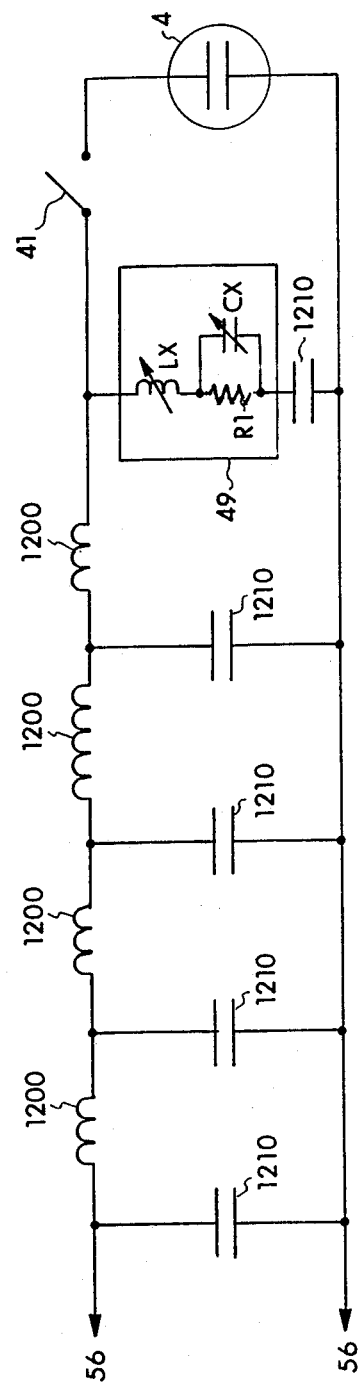
FIG. 12 is a schematic showing on alternate circuit for the charge accumulator of the present invention.

When the resistance of the pulse chamber 4 is known (i.e., when numerous suspensions of equal conductivity are to be processed), it is preferential to use a pulse-forming network of the type shown in FIG. 12 for the high voltage poration pulse. By doing so, there is no longer a need for a countdown timer 48 and a shorting switch 60. Only the switch 1220 (not shown) to connect the network to the pulse chamber 4 is needed.

The pulse length t, in microseconds, of such a network is:

$$t = n\sqrt{LC} \quad \text{(Formula 2)}$$

where:
n = the number of capacitors C
L = inductance in micro-Henries
C = capacitance in micro-Farads The resistance of the chamber 4 and the resistance R1 should be approximately equal. A small capacitance Cx may be added and should approximate the capacitance of the chamber.

The impedance of the network, Z $$\text{where } Z = \sqrt{L/C} \quad \text{(Formula 3)}$$

should be made equal to the resistance of the chamber (L is in microhemies and C is in microfarads).

The rise time in a high power system of this sort can then be controlled by the pulse shaper 49 as shown in FIG. 11 and discussed later.

In this case, the rise time of a pulse increases with increasing values of Cx and increases with decreasing values of Lx—both Cx and Lx being variable in this shaper 49. Cx is a high power vacuum capacitor. Lx is a single turn of bus wire where the inductance varies by moving a piece of magnetic core material in or out-of the one-turn inductor.

Under the teachings of the present invention, as shown in FIG. 11, the controllable rise time is an important factor for the uniform poration of the vesicles in the suspension. When the apparatus of the present invention is used t porate red blood cells, a fast rise time is necessitated as provided by pulse shaper 49. Specifically when red blood cells are exposed to an 8 KV/cm, 20 microsecond pulse with a controllable rise time of 5 microseconds no poration occurs. However, when red blood cells are exposed to the same 8 KV/cm, 20 microsecond pulse but with a controllable rise time (through adjustment 1130 of shaper 49) of 20 nanoseconds 1100 or less a high degree of poration occurs.

When trying to raise large quantities of high conductivity suspensions (1 ml–100 ml) to high electric field stress, the special switching techniques of the present invention are necessitated. The amount of current to raise the electric field across chamber 4 is even further increased by the fact that the chamber holding an aqueous solution acts as a capacitor and the water within the suspension acts as a dielectric (dielectric constant=80). As electric field is applied, the water, which is molecularly very polar molecule, begins to line up. The water molecules take a set time at a set temperature to line up and that time is about 250 nanoseconds at room temperature (20 degrees Celsius). Therefore, the capacitance "C", of a parallel plate pulse chamber filled with water where the electrode discs have a radius of 3.1 cm and are spaced apart by 0.33 cm (this chamber being one that holds 10 ml) is: therein $$C = Ke_o \frac{A}{d} = 0.07 \ \mu F \quad \text{(Formula 4)}$$

If we have to charge this to 333 volts (the voltage necessary to get 10 KV/cm) the charge, q, necessary in coulombs is:

$$\begin{aligned} q &= cv \quad \text{(Formula 5)} \\ &= 7 \times 10^{-8} \times 3.33 \times 10^3 \\ &= 23.3 \times 10^{-5} \text{ coulombs} \end{aligned}$$

If we have to charge up this capacitance in 233 nanoseconds, the average current, I, in amperes is:

$$\begin{aligned} q &= \mu t \quad \text{(Formula 6)} \\ &= \text{(current in amps)(time, seconds)} \end{aligned}$$

$$\begin{aligned} \text{Current in amps} = q/t &= \frac{2.33 \times 10^{-4} \text{ coulombs}}{2.33 \times 10^{-7} \text{ seconds}} \\ &= 1{,}000 \text{ amps} \end{aligned}$$

This is a dynamic change however with the original rate being about 2.5–3.0 times as large in a practical pulse circuit, the current tapering off over the charging duration. The necessary current to charge the capacitance is then in the order of 2500–3000 amperes over the first 30 or 40 nanoseconds.

The general resistance of the chamber with this volume of isotonically suspended cells is 2 ohms. At 3333 volts, by Ohms law, the field sustaining current is 1666 amperes. This would make the necessary current flow for rapid rise times to be:

Fast rise time current = capacitance current and sustaining current = 3000 + 1666 = 4666 amperes During the initial 30 or 40 nanoseconds, power would have to be delivered at a rate of about 12 megawatts (3333 volts×4666 amps). If there was just one tenth of an ohm in series with this current, there would be a voltage drop of 466 volts. This would mean a 13% decrease in the output voltage during the initial charging time, a value bordering on the unacceptable.

It has been found that the controllable rise time must be appreciably faster than 250 nanoseconds 1120 to realize poration of vesicles in highly conductive suspensions.

3. Toroidal Chamber

Figure 8:
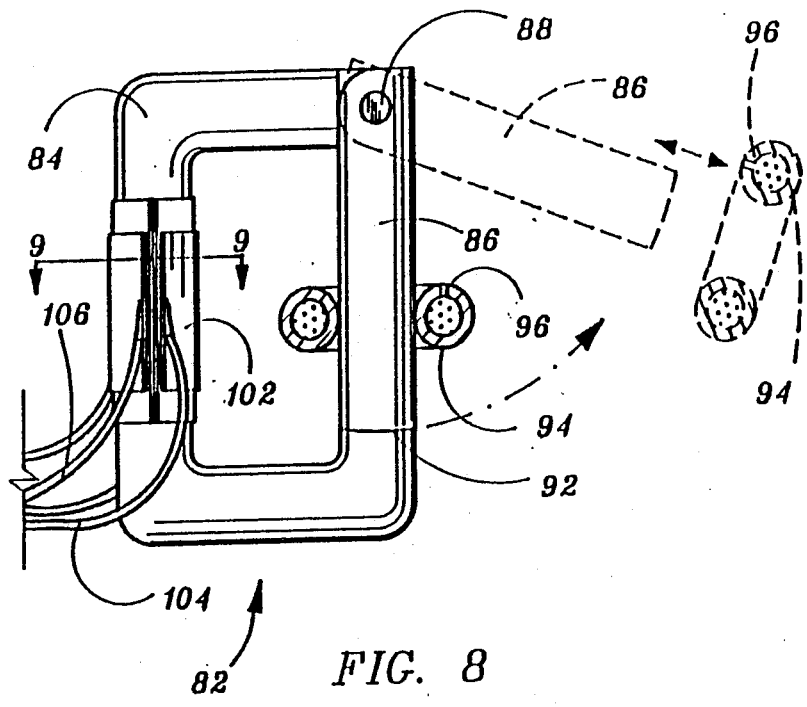
FIG. 8 is a representation, partially in cross-section, partially in phantom, of a modified system of the present invention for poration and fusion using magnetic fields.
Figure 9:
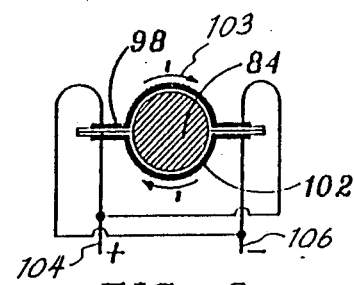
FIG. 9 is a cross-sectional view taken along line 9—9 of FIG. 8.
Figure 10:
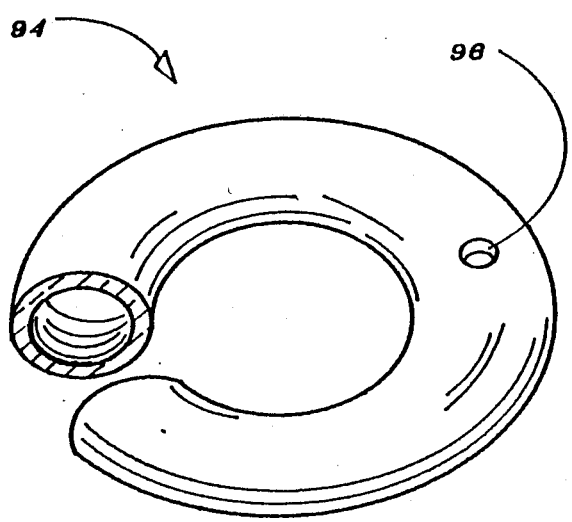
FIG. 10 is a perspective view, partially broken away, of a toroidal pulse chamber for use with the system of FIG. 8.

In an alternative embodiment of the present invention, poration and fusion of cells will be energized by magnetic means in a toroidal chamber. Referring to FIGS. 8, 9, and 10 there is shown magnetic core 82, including C-shaped conductive member 84, to which closure arm 86 will be swingably connected at pivot 88 and disconnectable at connecting point 92. When arm 86 is disconnected at connecting point 92, hollow toroidal chamber 94 will be capable of being slid onto or off of arm 86. Chamber 94 will be designed for the insertion and removal of "to-be-treated" electrolytic suspensions through fillhole 96. Half-wind current sheaths 98 and 102 will be wound on core 82, which sheaths, when current is applied with arm 86 closed, will induce magnetic flux around core 84 and arm 86. It is to be expressly understood, that the use of two sheaths is a preferred embodiment and that a single sheath by one skilled in the art could be utilized.

Wires 104 and 106 may be connected to a power system, such as that shown in FIG. 4, in place of chamber 1, with wires 104 and 106 electrically in series with high voltage electrode 44, and also to ground 70. The interconnection for the sheaths 98 and 102 are shown in FIG. 9. The operation of this magnetic system will be much like that set forth with regard to FIG. 4. In the operation of this magnetic system, current pulses 103 passing through the two half-sheaths 98 and 102 around core 84, will induce a large magnetic flux in the conductive material of core 84 and arm 86. This magnetic flux flowing through arm 86 will pass through the annulus of toroid 94 and induce a large electric field along the length of the solution contained in toroidal chamber 94 which is orthogonal to the core 84. This voltage pulse will be controlled, as in FIG. 6, and will be large enough to produce poration and/or fusion in the cells of the solution. This modified embodiment has the benefit of allowing the use of simple, inexpensive glass or plastic toroidal chambers 94, which chambers can be used once and then disposed of, without the need for electrodes or electrical wiring directly to the chambers. Hence, this embodiment provides an inexpensive chamber having many applications both in the laboratory and for industrial and commercial uses.

Finally, while a closed loop magnet is used in the preferred embodiment, it is to be expressly understood that an open loop magnetic system could be

EXAMPLES

Preparation of Red Blood Cells

Intact erythrocytes are isolated from freshly drawn heparinized blood by centrifugation at 1000×g for 10 minutes at 4 degrees C. The serum and buffy coat (other blood components) are then decanted from the top of the centrifuge tube. The erythrocytes or red blood cells are resuspended and recentrifuged in ten volumes of physiological saline. The foregoing procedure is repeated three times to wash away all other blood constituents. The washed erythrocytes are then resuspended in physiological saline, with the red blood cells occupying about one-tenth to one-half of the total volume.

The resulting suspension is then put in electrical pulse chamber 4 by means of a syringe through fillhole 18. The temperature of the suspension may be from about 4 degrees C. to about ambient temperature for poration, but the higher the temperature of the suspension, the shorter will be the time that the pores which will be electrically induced in the cells remain open. The pulse chamber is connected to a plug-in pulse module, not shown. The module is designed to be slid into a port in the front of the pulse apparatus to complete electrical connection to the module. In the following examples, "poration and loading" 2 ml of packed, washed human red blood cells are suspended in 8 ml phosphate buffered saline solution (PBS), a therein physiological saline well suited for maintaining the morphology of red blood cells. The resulting 10 milliliters of suspension is then injected into electrical pulse chamber 4 and chamber and suspension are cooled to a temperature of 4 degrees C.

First Example—Poration Loading

For poration of human red blood cells, in a pulse chamber having a 0.333 cm gap, typical pulse setting of 2666 volts for 40 microseconds having a controllable rise time of 10 nanoseconds is used. The rise time is controlled by pulse shaper 49. This provides an effective treatment of 8 KV/cm, i.e., 2666 V./0.333 cm. In operation, the cells are exposed to a frequency of 2 MHz for about 0.1 second at 100% duty cycle and field amplitude 33 V/cm to prealign the red blood cells. Then, 4 milliseconds later, an electroporation pulse of 2666 volts across the chamber 4, is administered for 40 microseconds. This represents an initial rise time power of 5.1 megawatts and a sustaining power of 3.53 megawatts. Following such treatment, the chamber containing the module is removed from the pulse apparatus port, and the pulse chamber is removed from the module. The suspended red blood cells are then removed from the chamber with a syringe and are found to be porated. The porated red blood cells are separated by centrifugation, and are then suspended in a media containing methotrexate, a 455 molecular weight chemotherapy drug. After such suspension a time of about 15 to 30 minutes is allowed to elapse. The suspension is heated to a temperature of 37 degrees C. to close or anneal the pores in the cell membrane. The cells are then washed by centrifuging and resuspending them three times in buffered physiological saline and are ready for use as a carrier for in-vivo injection and timed release of encapsulated drug into a patient's blood stream.

Typical loadings have injected about $5 \times 10^9$ molecules of methotrexate per red blood cell about twice the loadings obtained with poration without rotational pore-alignment.

Second Example—Poration

In this example, the use of the pulse forming network charge accumulator of FIG. 12 will be described. High frequency generator 64 is connected to the chamber by isolation switch 66. The high frequency voltage is applied at 33 volts for 0.1 seconds at a frequency of 2 MHz. During this time, the suspended cells align rotationally as shown in FIG. 7. Isolation switch 66 is then opened and as soon as the switch contacts have moved far enough apart to isolate the RF generator 64 the HV pulse switch 41 is closed. The chosen pulse is then applied. No count down timer 48 or shorting switch 60 is necessary when using a pulse forming network charge accumulator of FIG. 12. Identical results to previous example are realized in loading of red blood cells.

Third Example—Cell Fusion

The upper epidermis of leaves from light-grown, 6-day-old oat seedlings (Avena sativa, cv Victory) and 8-day-old corn seedlings (Zea mays, cv Bear Hybrid) are removed with fine forceps. The peeled leaves are then floated, upside down, on a solution containing 2% (w/v) Cellulysin (Calbiochem), 0.5 M containing 2% (w/v) Cellulysin (Calbipchem), 0.5 M mannitol, 3 mM CaCl2, mM KCl, and 3 mM Mes (morpholinoethanesulfonic acid) at pH 5.6. Digestion will then be complete after hours at 30 degrees C. in the dark. The protoplasts are then filtered through a nylon screen (pore diameter 80 μm), layered onto a 17% (w/v) sucrose pad, and centrifuged 10 min at 100 g. The protoplasts at the interface are collected, resuspended in 12 ml of 0.5 M mannitol and centrifuged for 3 minutes at 70 g. The pellet is then washed once with 0.5 M mannitol.

The oat protoplasts are then suspended in a 0.5 molar sucrose solution and are administered into the fusion/poration chamber with a syringe. The chamber is then connected into the pulse/fusion instrument as described above.

The protoplasts are then suspended with 10×cells per ml. and are treated at a frequency of 2 MHz applied at 70% duty cycle for 10 seconds at a field strength of 30 volts/cm to provide "bunching" or dielectrophoretic voltage. The duty cycle, amplitude time of the alignment voltage may be changed, but the net desired effect is to maximize the creation of cell pairs.

After the application of the bunching voltage, the isolation switch is allowed to open, then the poration/fusion pulse is applied. Poration of cells occurs and fusion occurs between cell pairs.

The bunching voltage is then reapplied and slowly ramped down over the next two minutes to hold fused cells in close contact and to keep lightly fused cells from coming back apart due to thermal, mechanical and other naturally occurring perturbations.

While preferred embodiments of the present invention have been shown, it is to be expressly understood that modifications and changes may be made thereto and that the present invention is set forth in the following claims.

I claim:

1. An apparatus for applying electric field pulses across a liquid suspension containing vesicles, said vesicles to be treated by said electric field pulses in said apparatus, said apparatus comprising:
   a hollow chamber for holding said liquid suspension, said chamber being formed of non-conductive material, said chamber being capable of being disposed of after said vesicles are treated,
   means in said chamber for the insertion and removal of said liquid suspension wherein said insertion and removal means is a formed hole in said chamber,
   a closed loop magnetic core, and
   means connected to said magnetic core for selectively energizing said magnetic core thereby causing magnetic flux to flow through said magnetic core, said magnetic core when energized providing a substantially uniform electrical field surrounding said magnetic core, said chamber containing said liquid suspension being held in said surrounding electrical field so that said electrical field pulses are applied to said vesicles for said vesicles when said chamber is held near said magnetic core by said holding means so that said electrical field pulses are applied to said vesicles for said treatment.

2. The apparatus of claim 1 wherein said magnetic core comprises two half wind current sheaths wound on said core to generate said magnetic flux.

3. An apparatus for applying electric field pulses across an electrolytic liquid suspension containing vesicles, said vesicles to be treated by said electric field pulses in said apparatus, said apparatus comprising:
   an electrically non-conductive hollow chamber for holding said electrolytic liquid suspension wherein said chamber is toroidal in shape, said chamber being capable of being disposed of after said vesicles are treated, means in said chamber for the insertion and removal of said electrolytic liquid suspension containing said vesicles, a magnetic core, means operative with said magnetic core and said chamber for releasably holding said chamber orthogonal to said magnetic core, and means connected to said magnetic core for selectively energizing said magnetic core thereby causing magnetic flux to flow through said magnetic core, said magnetic core when energized being capable of generating a substantially uniform electrical field across said chamber containing said electrolytic liquid suspension carrying said vesicles when said chamber is held near said magnetic core by said holding means so that said electrical field pulses are applied to said vesicles for said treatment.

4. The apparatus of claim 3 wherein said insertion and removal means is a formed hole in said chamber.

5. The apparatus of claim 3 wherein said magnetic core is a closed loop.

6. The apparatus of claim 5 wherein said magnetic core comprises two half wind current sheaths wound on said core to generate said magnetic flux.

7. An apparatus for applying electric field pulses across a liquid suspension containing vesicles, said vesicles to be treated by said electric field pulses in said apparatus, said apparatus comprising:

en electrically non-conductive hollow chamber for holding said liquid suspension, said chamber being formed inn a toroidal shape and having a center annulus region, means in said chamber for the insertion and removal of said liquid suspension containing said vesicles, a closed loop magnetic core, said magnetic core comprising:
(a) a C-shaped conductive member, and
(b) a closure arm having one end pivotally connected to one end of said C-shaped member, said closure arm having its other end releasably connectable to the other end of said C-shaped member, said annulus of said chamber being capable of sliding on and off over said closure arm when said closure arm is disconnected from said C-shaped member, said chamber being orthogonal to said closure arm when said chamber is slid over said closure arm, and said closure arm when connected to said C-shaped member completing a magnetic path around said magnetic core, means connected to said magnetic core for selectively energizing said magnetic core thereby causing magnetic flux to flow through said closure arm so that said electrical field pulses are applied across said chamber containing said liquid suspension carrying said vesicles when said chamber is oriented over said closure arm and when said closure arm is connected to said C-shaped member.

8. The apparatus of claim 7 wherein said chamber is formed of non-conductive material, said chamber being capable of being disposed of after said vesicles are treated.

9. The apparatus of claim 7 wherein said magnetic core comprises two half wind current sheaths wound on said core to generate said magnetic flux.

10. An apparatus for applying electric field pulses across a liquid suspension containing vesicles, said vesicles to be treated by said electric field pulses in said apparatus, said apparatus comprising:

an electrically non-conductive hollow chamber for holding said liquid suspension, said chamber being formed in a toroidal shape and having a center annulus region, said chamber being capable of being disposed of after said vesicles are treated, means in said chamber for the insertion and removal of said liquid suspension containing said vesicles, a closed loop magnetic core, said magnetic core comprising:
(a) a C-shaped conductive member, and
(b) a closure arm having one end pivotally connected to one end of said C-shaped member, said closure arm having its other end releasably connectable to the other end of said C-shaped member, said annulus of said chamber being capable of sliding on and off over said closure arm when said closure arm is disconnected from said C-shaped member, said chamber being orthogonal to said closure arm when said chamber is slid over said closure arm, and said closure arm when connected to said C-shaped member completing a magnetic path around said magnetic core,
(c) two half wind current sheaths would-therein around said C-shaped member and said closure arm, and means connected to said current sheaths wound on said magnetic core for selectively energizing said magnetic core thereby causing magnetic flux to flow through said closure are so that said electrical field pulses are applied across said chamber containing said liquid suspension carrying said vesicles when said chamber is oriented over said closure arm and when said closure arm is connected to said C-shaped member.

11. An apparatus for producing stable pores in and through membrane walls of vesicles contained in a liquid suspension, said apparatus comprising:

a chamber for holding said liquid suspension containing said vesicles, means in said chamber for the insertion and removal of said liquid suspension, means operative with said chamber for providing a substantially uniform electric field across said chamber containing said liquid suspension, wherein said providing means comprises:
(a) means connected to said delivering means for creating magnetic flux proportional to said charge, and
(b) means operative on said chamber for holding said chamber near said magnetic flux so that said chamber is oriented in said electric field created by said magnetic flux, means for generating a high voltage, high current charge, means connected to said generating means for selectively delivering said charge at a high speed rise time to said providing means so that immediate application of said charge to said providing means is obtained, said delivering means being selected from a group consisting of a moving spark gap, a gas filled spark gap, an ignition, a hot cathode hydrogen thyratron, a charge accumulator, a pulse forming network, and a cold cathode hydrogen thyratron, means connected to said delivering means for producing a variable pulse length to said charge, said producing means being capable of high speed termination of said charge to said providing means, said pulse length being sufficient to permit said charge to produce said stable pores in and through said membrane walls of said vesicles in said suspension, 12. An apparatus for producing stable pores in and through membrane walls of vesicles contained in a liquid suspension, said apparatus comprising:

a chamber for holding said liquid suspension containing said vesicles, means in said chamber for the insertion and removal of said liquid suspension, means operative with said chamber for providing a homogeneous electric field across said chamber containing said liquid suspension, means for generating a high voltage, high current charge of predetermined value, means connected to said generating means for selectively delivering said charge at a high speed rise time through a triggered ionization breakdown to said providing means to that immediate application of said charge to said producing means is obtained, wherein said providing means comprises:

(a) means connected to said delivering means for creating magnetic flux proportional to said change, and (b) means operative on said chamber for holding said chamber near said magnetic flux so that said chamber is oriented in said homogeneous electric field created by said magnetic flux, and means connected to said delivering means for producing a variable pulse length to said charge, said producing means being capable of high speed termination of said charge to said providing means, said pulse length being sufficient to permit said charge to produce said stable pores in and through said membrane walls of said vesicles in said suspension.

13. An apparatus for producing stable pores in and through membrane walls of vesicles contained in a liquid suspension, said apparatus comprising:

a chamber for holding said liquid suspension containing said vesicles, means in said chamber for the insertion and removal of said liquid suspension, a pair of parallel electrodes in said chamber spaced a predetermined distance apart on opposing ends of said chamber for providing a homogeneous electric field throughout said chamber containing said liquid suspension, each of said electrodes having the side facing the opposing electrode coated with an inert stable material to minimize electrolytic decomposition of said suspension containing said vesicles, means for generating a high voltage, high current charge of predetermined value, means connected to said generating means for selectively delivering said charge at a high speed rise time to said electrodes in said chamber so that immediate application of said charge to said electrodes is obtained, means connected to said chamber for matching the impedance of said chamber with said delivering means, and means connected to said delivering means for producing a variable pulse length to said charge, said producing means being capable of high speed shorting of said charge at the end of said pulse length thereby terminating said high voltage, high current charge between said electrodes, said pulse length being sufficient to permit said charge between said electrodes to produce said stable pores in and through said membrane walls of said vesicles in said suspension, the size of said pores being dependent upon (i) the value of said high voltage, (ii) said predetermined time length, and (iii) said high speed of said rise time and said termination of said charge across said electrode.

14. The apparatus of claim 13 wherein said matching means comprises an outer conductive cylinder around said chamber, said outer conductive cylinder being connected to one of said electrodes, each of said electrodes being coaxial to said outer conductive cylinder, said outer conductive cylinder being coaxially separated from said electrodes by said dielectric material.

15. An apparatus for the high speed application of high voltage, high current electric field pulses in a homogeneous electric field across a liquid suspension containing vesicles having membrane walls, said electric field pulses being capable of producing stable pores in and through said membrane walls of said vesicles, said apparatus comprising:

a chamber for holding said liquid suspension containing said vesicles, said chamber being capable of enduring autoclave temperatures and comprising:

(a) a pair of parallel electrodes spaced a predetermined distance apart on opposing ends of said chamber for providing said homogeneous electric field throughout said chamber, each of said electrodes having the side facing the opposing electrode coated with an inert stable material to minimize electrolytic decomposition of said suspension containing said vesicles, (b) dielectric material separating said electrodes for forming the sides of said chamber, and (c) means in said dielectric material for the insertion and removal of said liquid suspension, means connected to said chamber for matching the impedance of said chamber when said electric field pulses are applied wherein said matching means comprises an outer conductive cylinder around said chamber, said outer conductive cylinder being connected to one of said electrodes, each of said electrodes being coaxial to said outer conductive cylinder, said outer conductive cylinder being coaxially separated from said electrodes by said dielectric material, and means connected to said matching means and to said electrodes for applying said electric field pulses, said applying means comprising:

(a) means for generating a high voltage, high current charge of predetermined value, (b) means connected to said generating means for selectively delivering said charge at a high speed rise time to said electrodes in said chamber so that immediate application of said charge to said electrodes is obtained, (c) means connected to said delivering means for producing a pulse signal of variable length, said producing means being capable of high speed shorting of said charge at the end of said pulse length thereby terminating the application of said high voltage, high current charge between said electrodes by providing a high speed fall time to said charge, said pulse length being sufficient to permit said charge between said electrodes to produce said stable pores in and through said membrane walls of said vesicles in said suspension, the size of said pores being dependent upon (i) the value of said high voltage, (ii) said variable length, and (iii) said speed of rise time and said fall time of said charge across said electrodes.

16. An apparatus for producing stable pores in and through membrane walls of vesicles during poration of electrofusion contained in a liquid suspension, said apparatus comprising:

a chamber for holding said liquid suspension containing said vesicles, means in said chamber for the insertion and removal of said liquid suspension, means operative with said chamber for providing a homogeneous electric field across said chamber containing said liquid suspension wherein said providing means comprises:
 (a) means connected to said delivering means for creating magnetic flux proportional to said change, and
 (b) means operative on said chamber for holding said chamber near said magnetic flux so that said chamber is oriented in said homogeneous electric field created by said magnetic flux, means for generating a high power charge of greater than one megawatt, means connected to said generating means for selectively delivering said charge at a high speed rise time of less than fifty nanoseconds to said providing means so that immediate application of said charge to said producing means is obtained, and means connected to said delivering means for producing a variable pulse length, said producing means being capable of high speed termination of said charge to said providing means, said pulse length being sufficient to permit said charge to produce said stable pores in and through said membrane walls of said vesicles in said suspension.

17. An apparatus for producing stable pores in and through membrane walls of vesicles during poration or electrofusion contained in a liquid suspension, said apparatus comprising:

a chamber for holding more than one milliliter of said liquid suspension containing said vesicles, said liquid suspension being capable of being selected from the group consisting of electrolytic and non-electrolytic fluids, means in said chamber for the insertion and removal of said liquid suspension, means operative with said chamber for providing a homogeneous and uniform electric field across said chamber containing said liquid suspension so that all of said vesicles throughout said suspension in said chamber are simultaneously subjected to the same electric field potential, means connected to said providing means for generating a high power rectangular wave poration charge of greater than one megawatt, means connected to said generating means for selectively delivering said charge at a high speed rise time of less than fifth nanoseconds to said providing means so that immediate application of said charge to said producing means is obtained, said delivery means comprises means connected to said chamber for matching the impedance of said chamber with said delivery means, and means connected to said delivering means for producing a variable pulse length to said charge, said producing means being capable of high speed termination of said charge to said providing means, said pulse length being sufficient to permit said charge to produce said stable pores in and through said membrane walls of said vesicles in said suspension while maintaining the viability of said vesicles.

18. An apparatus for therein producing stable pores in and through membrane walls of vesicles during poration or electrofusion contained in a liquid suspension, said apparatus comprising:

a chamber for holding said liquid suspension containing said vesicles, means in said chamber for the insertion and removal of said liquid suspension, means for generating a high power charge of grater than one megawatt, means connected to said generating means for selectively delivering said charge at a high speed rise time of less than fifty nanoseconds to said providing means in said chamber so that immediate application of said charge to said providing means is obtained, said delivering means being capable of matching the impedance of said chamber wherein said impedance matching means comprises an outer conductive cylinder around said chamber, said outer conductive cylinder being connected to one of said electrodes, each of said electrodes being coaxial to said outer conductive cylinder, said outer conductive cylinder being coaxially separated from said electrodes by said dielectric material, means connected to said delivering means for producing a variable pulse length, said pulse length being sufficient to permit said charge between said electrodes to produce said stable pores in and through said membrane walls of said vesicles in said suspension, the size of said pores being dependent upon (i) the value of the voltage of said charge, (ii) said pulse length, and (iii) said high speed of said rise time of said charge across said providing means.

* * * * *